United States Patent [19]
Ebert et al.

[11] Patent Number: 5,843,149
[45] Date of Patent: Dec. 1, 1998

[54] ELECTRICAL LEAD INSULATOR

[75] Inventors: Michael J. Ebert, Fridley; Jennifer P. Miller, Elk River; James H. Vaughan, Blaine, all of Minn.

[73] Assignee: Medtronic, Inc., Minneapolis, Minn.

[21] Appl. No.: 740,341

[22] Filed: Nov. 7, 1996

[51] Int. Cl.⁶ ........................................ A61N 1/04
[52] U.S. Cl. ................................................ 607/116
[58] Field of Search ........................ 128/899; 607/1, 607/115, 116, 122, 129; 623/66

[56] References Cited

U.S. PATENT DOCUMENTS

| | | | |
|---|---|---|---|
| 4,033,355 | 7/1977 | Amundson | 607/122 |
| 4,643,202 | 2/1987 | Roche | 607/116 |
| 4,851,009 | 7/1989 | Pinchuk | 623/66 |
| 5,016,646 | 5/1991 | Gotthardt et al. | 607/122 |
| 5,198,033 | 3/1993 | Kelley et al. . | |
| 5,277,753 | 1/1994 | Kelley et al. . | |
| 5,375,609 | 12/1994 | Molacek et al. . | |
| 5,419,921 | 5/1995 | Molacek et al. . | |
| 5,538,510 | 7/1996 | Fontirroche et al. . | |

*Primary Examiner*—William E. Kamm
*Attorney, Agent, or Firm*—Reed A. Duthler; Harold R. Patton

[57] ABSTRACT

A lead insulator which provides resistance to tearing and/or abrasion for implantable flexible electrical lead insulators having a body of silicone elastomer material. A relatively thin layer of a second silicone is applied as an overcoat to a more substantial primary or first insulator body. The second silicone is more resistant to tearing and/or abrasion than the elastomer comprising the body of the insulator. Because tearing and/or abrasion are surface phenomena, only a relatively thin layer of the second material is particularly required and the mechanical properties of the primary material will determine the overall mechanical properties of the lead insulatior per se.

10 Claims, 1 Drawing Sheet

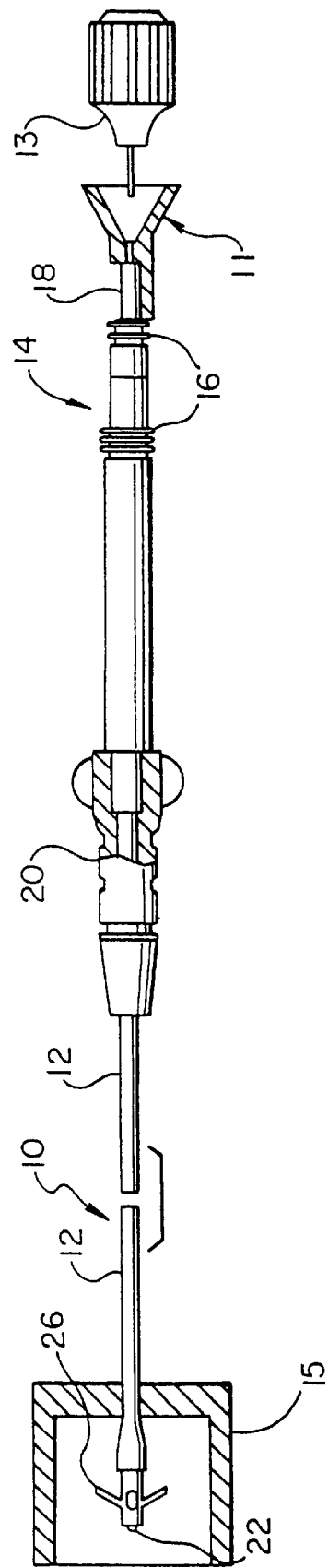

ELECTRICAL LEAD INSULATOR

BACKGROUND OF THE INVENTION

This invention relates to implantable prosthesis and to methods for making them less susceptible to degradation when implanted in vivo for extended periods of time. In its most preferred form, it concerns elastomeric silicone insulators for covering implantable electrical leads such as those used in cardiac pacing and the like.

Continuing efforts have been underway for sometime to develop elastomers for pacing lead insulators and the like. However, it is not yet clear whether any of these efforts will provide a biostable elastomer with desirable mechanical properties such as tearing and/or abrasion resistance.

Primary efforts have centered on the use of polyurethane elastomers as insulators. Some of these efforts, U.S. Pat. No. 4,851,009 issued to Pinchuk for example, employ a silicone rubber, typically a siloxane as a barrier coating over polyurethane to prevent in vivo cracking of the polyurethane. However, the application of silicone may require extensive treatments including the use of coupling agents, primer coats, exposure to free radical initiator and the like. In addition, placing silicone over the polyurethane tends to deprive the lead of some of the main advantages of the polyurethane.

It is an object of the invention to provide improved insulator covering material for implantable medical devices.

It is also an object of the present invention to provide an all silicone electrical lead insulator with improved resistance to in vivo degradation, tearing and/or abrasion.

It is also an object of the present invention to provide an electrical lead insulator having excellent flexibility and mechanical properties.

SUMMARY OF THE INVENTION

These and other objects have been accomplished by the present invention which, in its most preferred embodiment, takes the form of an insulator for electrical leads. It has been discovered that, where a flexible pacing lead insulator or the like has a body of a silicone elastomer, such as silicone tubing, is susceptible to tearing and/or abrasion when implanted in vivo over substantial time periods, a layer of a second silicone elastomer having different physical properties can be applied as an overcoat to provide a lead insulator with different physical properties, such as different stiffness, tear and/or abrasion resistance.

The overlayer may be applied by dip coating, spraying or co-extrusion to provide a desired combination of the properties of the two different silicone elastomer compositions. Also, since the composition employed for the base material and the overlayer material are both silicone elastomers, they have similar chemical and physical properties such that the second elastomer layer can be applied without the need for cumbersome and expensive surface treatment to the base silicone material.

The bulk of the insulator material may, in a preferred embodiment, be a soft elastomer having desired flexibility. A relatively thin layer of a second, more stiff and harder silicone elastomer provides favorable stiffness and tear and/or abrasion resistance to the overall lead structure.

Furthermore, in the case of silicone tubing, the lamination may overlay the base silicone tubing on the outside and additionally may be included on the inner lumen of the tubing or on the inside only or the outside only, depending on the desired properties.

BRIEF DESCRIPTION OF THE FIGURES

The sole FIGURE shows a side plan view of an endocardial uni-polar ball-tip electrode pacing lead making use of the bi-layer silicone insulator of the present invention.

DETAILED DESCRIPTION OF THE INVENTION

The present invention provides in its preferred embodiment a base or first layer of insulation of silicone elastomer, such as silicone tubing, coated with a second layer of silicone elastomer or equivalent, which may alter the stiffness of the overall insulator but which clearly imparts improved tear and/or abrasion resistance thereto. The insulation is intended primarily for use on electrical leads. In a most preferred form, the base silicone elastomer will be relatively soft tubing whereas the second layer is an overlayer of elastomer which may be relatively hard and stiff. Various combinations of physical and mechanical properties and relative thicknesses will be readily selected to obtain desired overall physical and mechanical properties according to the properties of the two silicones used. As already pointed out, the first layer is preferably in the form of tubing and the second layer is typically an overcoat thereon. However, it could be placed on the inner surface of the tubing if desired even though the second layer is referred to hereinafter as an overlayer. In the most preferred embodiment the base insulation will be silicone tubing such as MED-4516 or 4719 (NuSil Technology of Carpinteria, California) or MDX-4516 (Dow Corning Corporation of Midland, Mich.) having for example a wall thickness of about 0.005 inches and a coating thereon about 0.003–0.005 inches thick of silicone such as MED4720 (NuSil) or polyurethane 75D. The hardness of the coating is about 20A to 75D. MDX silicones are peroxide cured silicone rubbers. HP silicones from Dow Corning are also useful. They are high performance silicone rubbers.

Table 1 includes additional examples

TABLE 1

STIFFNESS OF CO-EXTRUDED PACING LEAD INSULATION

| COATING THICKNESS (in) | TUBE ELASTIC MODULUS ($E_1$) | COATING ELASTIC MODULUS ($E_2$) | TUBE INSIDE DIAMETER $d_1$ (in) | TUBE OUTSIDE DIAMETER $d_2$ (in) | COATING OUTSIDE DIAMETER $d_3$ (in) | STIFFNESS COMPOSITE (EI × $10^4$) |
|---|---|---|---|---|---|---|
| All 4516 (Base Tube/No Coat.) | 600 | | .073 | .101 | | 22.3 |
| .002-(4720) | 600 | 70 | .073 | .097 | .101 | 18.2 |
| .004-(4720) | 600 | 70 | .073 | .093 | .101 | 14.7 |

TABLE 1-continued

STIFFNESS OF CO-EXTRUDED PACING LEAD INSULATION

| COATING THICKNESS (in) | TUBE ELASTIC MODULUS ($E_1$) | COATING ELASTIC MODULUS ($E_2$) | TUBE INSIDE DIAMETER $d_1$ (in) | TUBE OUTSIDE DIAMETER $d_2$ (in) | COATING OUTSIDE DIAMETER $d_3$ (in) | STIFFNESS COMPOSITE (EI × $10^4$) |
|---|---|---|---|---|---|---|
| .008-(4720) | 600 | 70 | .073 | .085 | .101 | 8.8 |
| All 4720 (Base Tube/No Coat.) |  | 70 | .073 | .101 |  | 2.6 |

Crush resistance testing of the examples in Table 1 was performed by dynamically compressing the silicone tubing under a defined consistent percent compression relative to the cross sectional width of the tubing. The cycles of the compression were measured and recorded until the tubing split. The tubing was evaluated for abrasion after the samples had failed. In these tests the MDX4-4516 (Dow Corning) silicone controls split after 800 cycles with a moderate amount of abrasion. The same size tubing made from Q7-4720 (Dow Corning) silicone split after 30 cycles and continued on test until the controls failed. The Q7-4720 showed very little surface abrasion. A composite of MDX4-4516 as the base and a coating of Q7-4720 would impart the resistance of splitting of the MDX4-4516 and the abrasion resistance of the Q7-4720.

Methods of Application

The application of the second material layer to the first layer may be accomplished by using any of the existing well known methods including dipping, spraying, and co-extrusion, with co-extrusion being preferred. Coating of polymeric biomedical devices by dipping, spraying, or co-extrusion techniques are known to those skilled in the art. Consequently, they need not described in detail herein.

The layer of the second material in a preferred embodiment for pacing leads should generally be in the range of about 0.0005 to 0.010 inches in thickness, although it may be thinner or thicker depending on the application needs.

Likewise, the first layer for a pacemaker lead should generally be in the range of about 0.0005 to 0.010 inches in thickness, although it may be thinner or thicker depending on the application needs.

Acceptable Compositions For Second Layer

The most preferred second, overlaying material will be a silicone elastomer and may be platinum catalyzed, tin catalyzed or peroxide catalyzed all of which are known and familiar in the art. Likewise, the same is true of the first layer of silicone material.

The acceptable second layer, for lead insulation, will preferably have a hardness of about 20-85A. Suitable exemplary compositions in addition to silicones include acrylics and polyurethanes although silicone is most preferred at present as already stated.

Implantable Devices

Modified stiffness, tear and/or abrasion resistance may be achieved with many implantable medical devices. Such medical devices can include insulator sheaths of cardiac pacemaker leads, artificial heart diaphragms, artificial heart valve leaflets, sewing cuffs and the like. However, the preferred use of the invention is to provide improved resistance to tearing and abrasion in critical electrical lead insulation applications. In a typical lead and lead insulator assembly, a bi-layer silicone elastomeric insulator of the invention is the outer element through which coiled conductors pass. The configuration can include separate, mutually insulated coils in which the multiple coils are carried in separate insulator passages in co-axial or side by side arrangement or multi-polar coiled conductors having individually insulated coil wires which pass through an outer insulator sheath of bi-layer silicone elastomer. Similar configured lead systems are disclosed in greater detail in U.S. Pat. No. 5,040,544 issued to Lessar et al. although different elastomer compositions are described. In such lead systems, the silicone lead insulator is essentially an extruded piece of tubing of the desired shape and size required to carry the conductors. An outside diameter of the insulator may typically be in the range of about 0.02–0.25 inches with a wall thickness typically in the range of about 0.004 to 0.020 inches. To obtain the bi-layer construction of the invention, co-extrusion will preferably be used in forming the insulator as extruded tubing.

For detailed description, the FIGURE illustrates a plan view of an exposed electrode constructed in accordance with the present invention. The lead includes an elongated lead body generally indicated at 10 covered by an insulative sleeve 12. Insulative sleeve or insulator 12 is fabricated of a bi-layer silicone rubber according to the invention. At the proximal end of the lead, terminal assembly 14 is adapted to couple the lead to an implantable pacemaker pulse generator. Terminal assembly 14 is provided with sealing ring 16 and a terminal pin 18, all of a type known in the art. An anchoring sleeve 20 (shown partially in cross-section) slides over the lead body 10 and serves as a point for suturing the lead body to body tissue at the insertion point of the lead into the vein or tissue in a fashion known in the art. Anchoring sleeve 20 and terminal assembly 14 may be conveniently fabricated of bi-layer silicone rubber or elastomer according to the invention also. For purposes of definition, when the term insulator is utilized in this specification, it is to be taken as generally meaning any configuration of bi-layer silicone or the like according to the invention utilized to cover in whole or in part an implantable device, preferably an electrical lead which may include one or more such insulator coverings in whole or in part.

The lead shown in the FIGURE further includes a stylet guide 11 and stylet assembly 13 coupled to the terminal pin 18 for imparting stiffness to the lead during the insertion and placement of the lead transvenously into either the right ventricle or the right atrium of the heart. The stylet members are discarded after use and before connection of a terminal pin 18 to a pacemaker pulse generator.

At the distal end of the lead 10, a tine protector 15 is shown protecting the tines until the lead is used. Tines 26 are employed to passively retain the tip electrode 22 in position against the endocardium as is well known in the pacing art.

The lead assembly 10 of the FIGURE includes a multifiler conductor coil or body extending from the terminal pin 18 to the tip electrode 22. The FIGURE depicts a uni-polar lead and it should be understood that the present invention may be implemented in bi-polar lead designs and in other electrical implantable lead designs for any implantable medical device including devices other than pacemakers per se. The particular lead disclosed in the FIGURE is described and included for exemplification only.

The effect of using an overlaying material of differing mechanical properties from an inner layer can be easily calculated for a pacing lead insulator.

$$(EI)_{COMPOSITE} = \pi \frac{E_1}{64} (d_2^4 - d_1^4) + \pi \frac{E_2}{64} (d_3^4 - d_2^4)$$

For a composition tube having an inner, base material and an overlaying, outer material, the following formula can be applied:

Where E is the elastic modulus of the base material, $E_2$ is the elastic modulus of the overlaying material, $d_1$ is the inside diameter of the base material, $d_2$ is the outside diameter of the base material and the inside diameter of the overlaying material, and $d_3$ is the outside diameter of the overlaying material. Therefore, if one wished to provide a pacing insulator lead with a base material of silicone having an overlaying layer of another silicone, the relative overall stiffness of the lead insulator would be readily determined.

While this invention may be embodied in many different forms, specific preferred embodiments are described in detail herein. The description is an exemplification of the principles of the invention and is not intended to limit the invention to the particular embodiments illustrated.

What is claimed is as follows:

1. An insulator for implantable medical devices, comprised of first and second layers of different silicone elastomer having different physical and mechanical properties, wherein the first layer is an inner layer and the second layer is an outer layer and wherein the first layer is a silicone elastomer of composition MED-4516 and the second layer is a silicone elastomer of composition MED-4720.

2. The device of claim 1 in tubular form as a flexible electrical lead insulator.

3. The article of claim 1 wherein the second layer is thinner than the first layer.

4. An implantable electrical lead comprised of an elongated conductor and a tubular insulative lead body covering at least a portion of the conductor, the lead body being comprised of at least two layers of different silicone elastomer having different physical and mechanical properties, wherein the lead body comprises an inner layer taking the form of an elongated tube and an outer layer surrounding the inner layer, the outer layer being stiffer than the inner layer.

5. A lead according to claim 4 wherein the outer layer has greater stiffness than the inner layer.

6. An implantable electrical lead comprised of an elongated conductor and a tubular insulative lead body covering at least a portion of the conductor, the lead body being comprised of at least two layers of different silicone elastomer having different physical and mechanical properties, wherein the lead body comprises an inner layer taking the form of an elongated tube and an outer layer surrounding the inner layer, the outer layer being thinner than the inner layer and having greater stiffness than the inner layer.

7. An implantable electrical lead comprised of an elongated conductor and a tubular insulative lead body covering at least a portion of the conductor, the lead body being comprised of at least two layers of different silicone elastomer having different physical and mechanical properties, wherein the lead body comprises an inner layer taking the form of an elongated tube and an outer layer surrounding the inner layer, the outer layer having greater stiffness than the inner layer and having greater hardness than the inner layer.

8. A lead according to claim 7 wherein the inner layer is a silicone elastomer of composition MED-4516 and the outer layer is a silicone elastomer of composition MED-4720.

9. An implantable electrical lead comprised of an elongated conductor and a tubular insulative lead body covering at least a portion of the conductor, the lead body being comprised of at least two layers of different silicone elastomer having different physical and mechanical properties, wherein the lead body comprises an inner layer taking the form of an elongated tube and an outer layer surrounding the inner layer, the outer layer being stiffer than the inner layer.

10. An implantable electrical lead comprised of an elongated conductor and a tubular insulative lead body covering at least a portion of the conductor, the lead body being comprised of at least two layers of different silicone elastomer having different physical and mechanical properties, wherein the lead body comprises an inner layer taking the form of an elongated tube and an outer layer surrounding the inner layer, the outer layer being thinner than the inner layer and having greater hardness than the inner layer.

* * * * *